(12) United States Patent
Campbell et al.

(10) Patent No.: US 8,449,625 B2
(45) Date of Patent: May 28, 2013

(54) METHODS OF MEASURING HEART VALVE ANNULUSES FOR VALVE REPLACEMENT

(75) Inventors: Louis A. Campbell, Santa Ana, CA (US); Travis Z. Oba, Corona, CA (US); Rafael Pintor, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 508 days.

(21) Appl. No.: 12/606,945

(22) Filed: Oct. 27, 2009

(65) Prior Publication Data
US 2011/0098602 A1 Apr. 28, 2011

(51) Int. Cl.
*A61B 17/00* (2006.01)
*A61B 18/00* (2006.01)

(52) U.S. Cl.
USPC .......................................... 623/904; 600/587

(58) Field of Classification Search
USPC ...... 600/587, 590–591; 623/2, 900, 2.1–2.42, 623/902–904, 912–913, 918, 920, 922; 604/104; 606/194; 33/511–512
See application file for complete search history.

(56) References Cited

U.S. PATENT DOCUMENTS

| | | | |
|---|---|---|---|
| 3,143,742 A | | 8/1964 | Cromie |
| 3,164,009 A | * | 1/1965 | Marsh et al. ................ 73/789 |
| 3,320,972 A | | 5/1967 | High et al. |
| 3,371,352 A | | 3/1968 | Siposs et al. |
| 3,546,710 A | | 12/1970 | Shumakov et al. |
| 3,574,865 A | | 4/1971 | Hamaker |
| 3,755,823 A | | 9/1973 | Hancock |
| 3,839,741 A | | 10/1974 | Haller |
| 3,997,923 A | | 12/1976 | Possis |
| 4,016,867 A | | 4/1977 | King |
| 4,035,849 A | | 7/1977 | Angell et al. |
| 4,078,468 A | | 3/1978 | Civitello |
| 4,079,468 A | | 3/1978 | Liotta et al. |
| 4,084,268 A | | 4/1978 | Ionexcu et al. |
| 4,106,129 A | | 8/1978 | Carpentier et al. |
| 4,172,295 A | | 10/1979 | Batten |
| 4,185,638 A | * | 1/1980 | Bruner ................ 604/100.01 |
| 4,217,665 A | | 8/1980 | Bex |
| 4,218,782 A | | 8/1980 | Rygg |
| 4,259,753 A | | 4/1981 | Liotta et al. |
| RE30,912 E | | 4/1982 | Hancock |
| 4,343,048 A | | 8/1982 | Ross et al. |
| 4,362,167 A | | 12/1982 | Nicolai |
| 4,364,126 A | | 12/1982 | Rosen et al. |

(Continued)

FOREIGN PATENT DOCUMENTS
EP 0 084 395 8/1986
EP 0 096 721 12/1987

(Continued)

OTHER PUBLICATIONS

International Search Report from corresponding PCT Application No. PCT/IB2009/007785 dated Jun. 10, 2010.

(Continued)

*Primary Examiner* — Rene Towa
(74) *Attorney, Agent, or Firm* — AnneMarie Kaiser; Guy Cumberbatch

(57) ABSTRACT

A device for measuring an expanded internal orifice of a patient includes an orifice-expanding device, a pressure measuring device, and a size-measuring device. The size-measuring device measures a dimension of the orifice after it has been expanded by the orifice-expanding device.

28 Claims, 11 Drawing Sheets

U.S. PATENT DOCUMENTS

| | | | |
|---|---|---|---|
| 4,388,735 A | 6/1983 | Ionescu et al. | |
| 4,441,216 A | 4/1984 | Ionescu et al. | |
| 4,451,936 A | 6/1984 | Carpentier et al. | |
| 4,470,157 A | 9/1984 | Love | |
| 4,501,030 A | 2/1985 | Lane | |
| 4,506,394 A | 3/1985 | Bedard | |
| 4,535,483 A | 8/1985 | Klawitter et al. | |
| 4,566,465 A * | 1/1986 | Arhan et al. | 600/591 |
| 4,605,407 A | 8/1986 | Black et al. | |
| 4,626,255 A | 12/1986 | Reichart et al. | |
| 4,629,459 A | 12/1986 | Ionescu et al. | |
| 4,643,194 A | 2/1987 | Fogarty | |
| 4,680,031 A | 7/1987 | Alonso | |
| 4,705,516 A | 11/1987 | Barone et al. | |
| 4,725,274 A | 2/1988 | Lane et al. | |
| 4,731,074 A | 3/1988 | Rousseau et al. | |
| 4,778,461 A | 10/1988 | Pietsch et al. | |
| 4,790,843 A | 12/1988 | Carpentier et al. | |
| 4,851,000 A | 7/1989 | Gupta | |
| 4,888,009 A | 12/1989 | Lederman et al. | |
| 4,960,424 A | 10/1990 | Grooters | |
| 5,010,892 A | 4/1991 | Colvin | |
| 5,032,128 A | 7/1991 | Alonso | |
| 5,037,434 A | 8/1991 | Lane | |
| 5,147,391 A | 9/1992 | Lane | |
| 5,163,955 A | 11/1992 | Love et al. | |
| 5,258,023 A | 11/1993 | Reger | |
| 5,326,370 A | 7/1994 | Love et al. | |
| 5,326,371 A | 7/1994 | Love et al. | |
| 5,332,402 A | 7/1994 | Teitelbaum | |
| 5,376,112 A | 12/1994 | Duran | |
| 5,397,351 A | 3/1995 | Pavcnik et al. | |
| 5,423,887 A | 6/1995 | Love et al. | |
| 5,425,741 A | 6/1995 | Lemp et al. | |
| 5,431,676 A | 7/1995 | Dubrul et al. | |
| 5,449,384 A | 9/1995 | Johnson | |
| 5,449,385 A | 9/1995 | Religa et al. | |
| 5,469,868 A | 11/1995 | Reger | |
| 5,488,789 A | 2/1996 | Religa et al. | |
| 5,489,297 A | 2/1996 | Duran | |
| 5,489,298 A | 2/1996 | Love et al. | |
| 5,500,016 A | 3/1996 | Fisher | |
| 5,549,665 A | 8/1996 | Vesely et al. | |
| 5,562,729 A | 10/1996 | Purdy et al. | |
| 5,571,215 A | 11/1996 | Sterman et al. | |
| 5,578,076 A | 11/1996 | Krueger et al. | |
| 5,584,803 A | 12/1996 | Stevens et al. | |
| 5,618,307 A | 4/1997 | Donlon et al. | |
| 5,626,607 A | 5/1997 | Malecki et al. | |
| 5,628,789 A | 5/1997 | Vanney et al. | |
| 5,693,090 A | 12/1997 | Unsworth et al. | |
| 5,695,503 A | 12/1997 | Krueger et al. | |
| 5,713,952 A | 2/1998 | Vanney et al. | |
| 5,716,370 A | 2/1998 | Williamson, IV et al. | |
| 5,728,151 A | 3/1998 | Garrison et al. | |
| 5,735,894 A | 4/1998 | Krueger et al. | |
| 5,752,522 A | 5/1998 | Murphy | |
| 5,755,782 A | 5/1998 | Love et al. | |
| 5,766,240 A | 6/1998 | Johnson | |
| 5,800,527 A | 9/1998 | Jansen et al. | |
| 5,814,097 A | 9/1998 | Sterman et al. | |
| 5,814,098 A * | 9/1998 | Hinnenkamp et al. | 335/12 |
| 5,824,064 A | 10/1998 | Taheri | |
| 5,840,081 A | 11/1998 | Andersen et al. | |
| 5,855,601 A | 1/1999 | Bessler et al. | |
| 5,891,160 A | 4/1999 | Williamson, IV et al. | |
| 5,895,420 A | 4/1999 | Mirsch, II et al. | |
| 5,908,450 A | 6/1999 | Gross et al. | |
| 5,957,949 A | 9/1999 | Leonhardt et al. | |
| 5,972,004 A | 10/1999 | Williamson, IV et al. | |
| 5,984,959 A | 11/1999 | Robertson et al. | |
| 5,984,973 A | 11/1999 | Girard et al. | |
| 6,010,511 A * | 1/2000 | Murphy | 606/108 |
| 6,010,531 A | 1/2000 | Donlon et al. | |
| 6,042,607 A | 3/2000 | Williamson, IV et al. | |
| 6,066,160 A | 5/2000 | Colvin et al. | |
| 6,074,418 A | 6/2000 | Buchanan et al. | |
| 6,106,550 A | 8/2000 | Magovern et al. | |
| 6,162,233 A | 12/2000 | Williamson, IV et al. | |
| 6,168,614 B1 | 1/2001 | Andersen et al. | |
| 6,176,877 B1 | 1/2001 | Buchanan et al. | |
| 6,197,054 B1 | 3/2001 | Hamblin, Jr. et al. | |
| 6,217,611 B1 | 4/2001 | Klostermeyer | |
| 6,231,561 B1 | 5/2001 | Frazier et al. | |
| 6,241,765 B1 | 6/2001 | Griffin et al. | |
| 6,245,102 B1 | 6/2001 | Jayaraman | |
| 6,283,127 B1 | 9/2001 | Sterman et al. | |
| 6,287,339 B1 | 9/2001 | Vazquez et al. | |
| 6,290,674 B1 | 9/2001 | Roue et al. | |
| 6,312,447 B1 | 11/2001 | Grimes | |
| 6,312,465 B1 | 11/2001 | Griffin et al. | |
| 6,319,281 B1 * | 11/2001 | Patel | 623/2.3 |
| 6,322,526 B1 | 11/2001 | Rosenman | |
| 6,328,727 B1 | 12/2001 | Frazier et al. | |
| 6,350,281 B1 | 2/2002 | Rhee | |
| 6,371,983 B1 | 4/2002 | Lane | |
| 6,402,780 B2 | 6/2002 | Williamson, IV et al. | |
| 6,425,916 B1 | 7/2002 | Garrison et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,468,305 B1 | 10/2002 | Otte | |
| 6,582,419 B1 | 6/2003 | Schoon | |
| 6,582,462 B1 | 6/2003 | Andersen et al. | |
| 6,585,766 B1 | 7/2003 | Huynh et al. | |
| 6,598,307 B2 | 7/2003 | Love | |
| 6,652,578 B2 | 11/2003 | Bailey et al. | |
| 6,685,739 B2 | 2/2004 | DiMatteo et al. | |
| 6,730,118 B2 | 5/2004 | Spenser et al. | |
| 6,733,525 B2 | 5/2004 | Yang et al. | |
| 6,764,508 B1 | 7/2004 | Roeche et al. | |
| 6,767,362 B2 | 7/2004 | Schreck | |
| 6,786,925 B1 | 9/2004 | Schoon et al. | |
| 6,790,229 B1 | 9/2004 | Berreklouw | |
| 6,790,230 B2 | 9/2004 | Beyersdorf et al. | |
| 6,805,711 B2 | 10/2004 | Quijano et al. | |
| 6,893,459 B1 | 5/2005 | Macoviak | |
| 6,893,460 B2 | 5/2005 | Spenser et al. | |
| 6,908,481 B2 | 6/2005 | Cribier | |
| 6,939,365 B1 | 9/2005 | Fogarty et al. | |
| 6,942,694 B2 | 9/2005 | Liddicoat | |
| 7,011,681 B2 | 3/2006 | Vesely | |
| 7,025,780 B2 | 4/2006 | Gabbay | |
| 7,070,616 B2 | 7/2006 | Majercak et al. | |
| 7,097,659 B2 | 8/2006 | Woolfson et al. | |
| 7,101,396 B2 | 9/2006 | Artof et al. | |
| 7,147,663 B1 | 12/2006 | Berg et al. | |
| 7,153,324 B2 | 12/2006 | Case et al. | |
| 7,195,641 B2 | 3/2007 | Palmaz et al. | |
| 7,201,771 B2 | 4/2007 | Lane | |
| 7,201,772 B2 | 4/2007 | Schwammenthal et al. | |
| 7,238,200 B2 | 7/2007 | Lee et al. | |
| 7,252,682 B2 | 8/2007 | Seguin | |
| 7,258,698 B2 | 8/2007 | Lemmon | |
| 7,261,732 B2 | 8/2007 | Justino | |
| RE40,377 E | 6/2008 | Williamson, IV et al. | |
| 7,422,603 B2 | 9/2008 | Lane | |
| 7,513,909 B2 | 4/2009 | Lane | |
| 7,556,647 B2 | 7/2009 | Drews et al. | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0049492 A1 | 12/2001 | Frazier et al. | |
| 2002/0026238 A1 | 2/2002 | Lane et al. | |
| 2002/0032481 A1 | 3/2002 | Gabbay | |
| 2002/0058995 A1 | 5/2002 | Stevens | |
| 2002/0123802 A1 | 9/2002 | Snyders | |
| 2002/0138138 A1 | 9/2002 | Yang | |
| 2002/0151970 A1 | 10/2002 | Garrison et al. | |
| 2002/0188348 A1 | 12/2002 | DiMatteo et al. | |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0036795 A1 | 2/2003 | Andersen et al. | |
| 2003/0040792 A1 | 2/2003 | Gabbay | |

| | | |
|---|---|---|
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0191416 A1 | 10/2003 | Rosenman et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson, IV et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0215235 A1 | 10/2004 | Jackson et al. |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0064039 A1 | 3/2006 | Griego et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195134 A1 | 8/2006 | Crittendon |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0246888 A1 | 11/2006 | Bender et al. |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2007/0299513 A1* | 12/2007 | Ryan et al. .................. 623/2.36 |
| 2008/0009746 A1 | 1/2008 | Forster et al. |
| 2008/0033543 A1 | 2/2008 | Gurskis et al. |
| 2008/0119875 A1 | 5/2008 | Ino et al. |
| 2008/0319543 A1 | 12/2008 | Lane |
| 2009/0036903 A1 | 2/2009 | Ino et al. |
| 2009/0069890 A1* | 3/2009 | Suri et al. .................... 623/2.11 |
| 2009/0132036 A1 | 5/2009 | Navia |
| 2009/0182419 A1* | 7/2009 | Bolling ....................... 623/2.36 |
| 2009/0192599 A1 | 7/2009 | Lane et al. |
| 2009/0192600 A1* | 7/2009 | Ryan ........................... 623/2.11 |
| 2009/0192603 A1 | 7/2009 | Ryan |
| 2009/0192604 A1 | 7/2009 | Gloss |
| 2010/0152844 A1* | 6/2010 | Couetil ....................... 623/2.36 |

FOREIGN PATENT DOCUMENTS

| | | |
|---|---|---|
| EP | 0 125 393 | 12/1987 |
| EP | 0 179 562 | 7/1989 |
| EP | 0 143 246 | 11/1991 |
| EP | 1171059 | 1/2002 |
| EP | 2080474 A1 | 7/2009 |
| GB | 2 056 023 | 3/1981 |
| GB | 2 069 843 | 9/1981 |
| GB | 2137499 | 10/1984 |
| GB | 2254254 | 10/1992 |
| GB | 2 279 134 | 12/1994 |
| SU | 1116573 | 7/1985 |
| WO | 89/00084 | 2/1989 |
| WO | 91/15167 | 10/1991 |
| WO | 92/01269 | 8/1992 |
| WO | 92/13502 | 8/1992 |
| WO | 92/19184 | 11/1992 |
| WO | 92/19185 | 11/1992 |
| WO | 95/28899 | 11/1995 |
| WO | 97/27799 | 1/1997 |

| | | |
|---|---|---|
| WO | 97/09933 | 3/1997 |
| WO | 97/09944 | 3/1997 |
| WO | 99/15112 | 4/1999 |
| WO | 00/60995 | 10/2000 |
| WO | 2006/086135 | 8/2006 |
| WO | WO2010090720 A1 | 8/2010 |

OTHER PUBLICATIONS

Extended Search Report in corresponding international application No. 09179532.8-2319 dated Dec. 18, 2012.

* cited by examiner

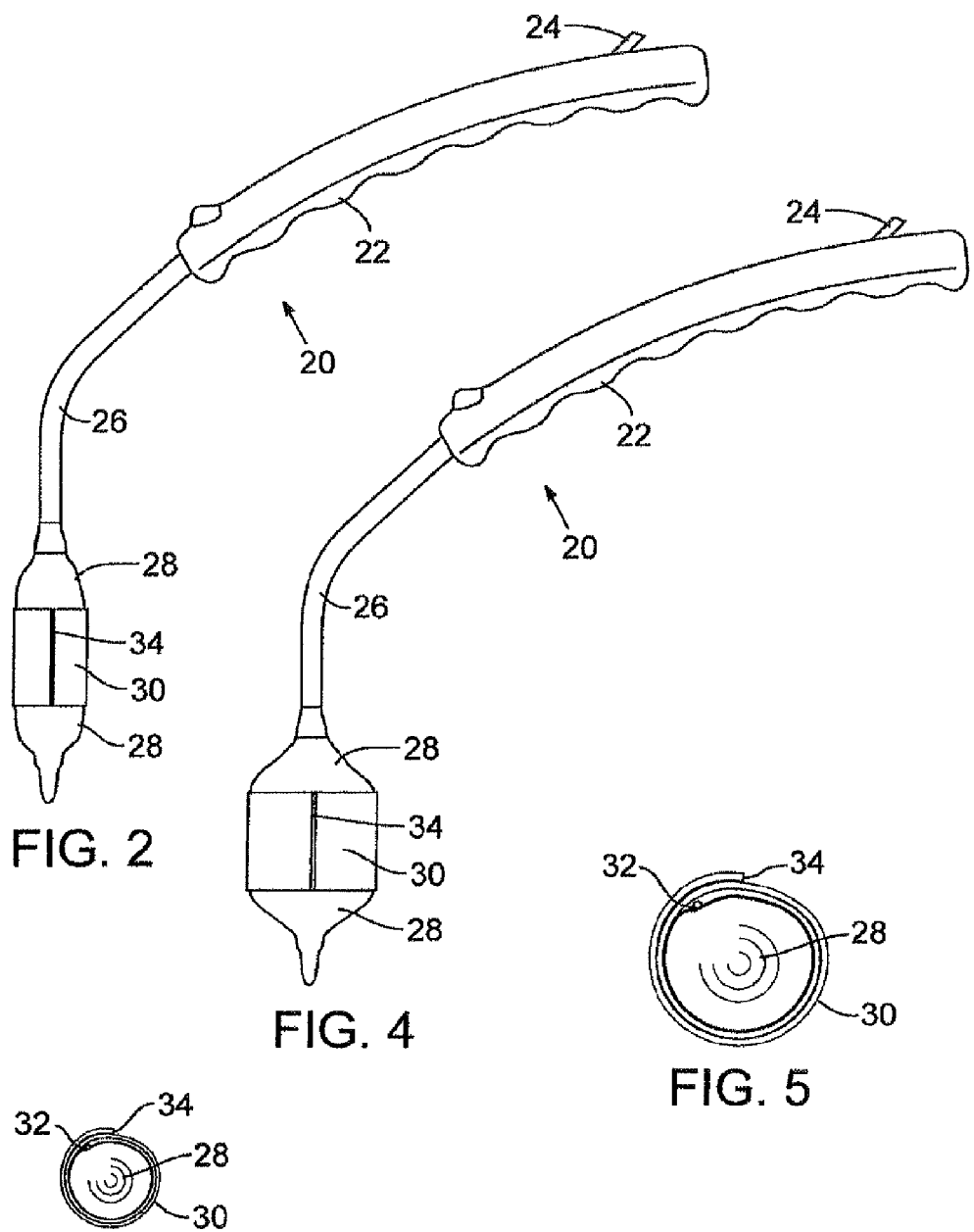
FIG. 2
FIG. 4
FIG. 5
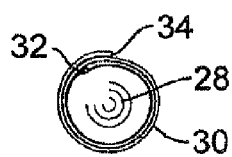
FIG. 3

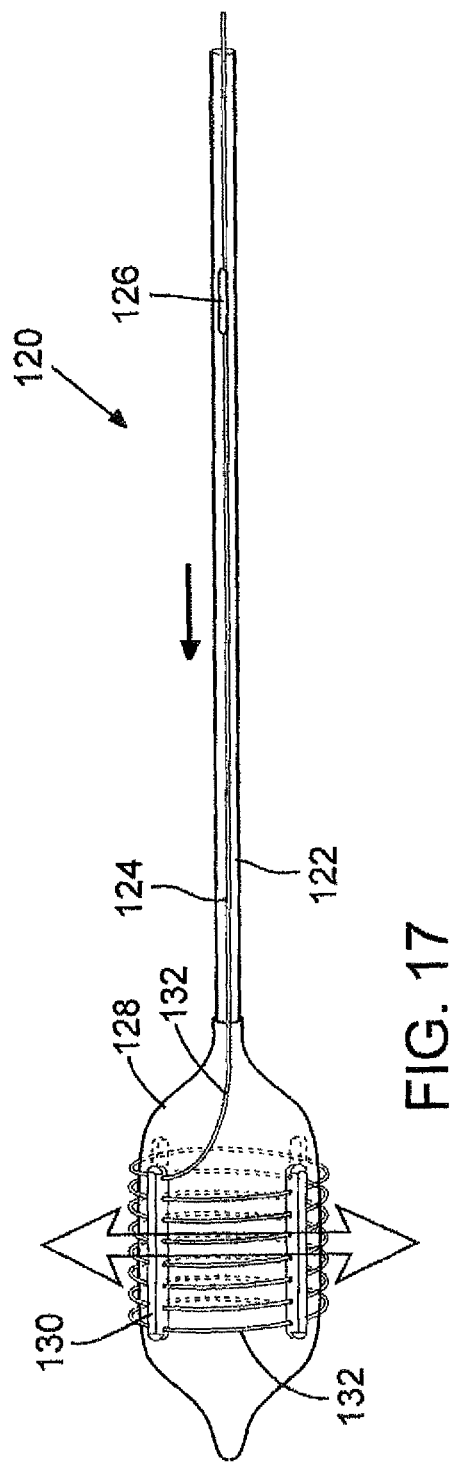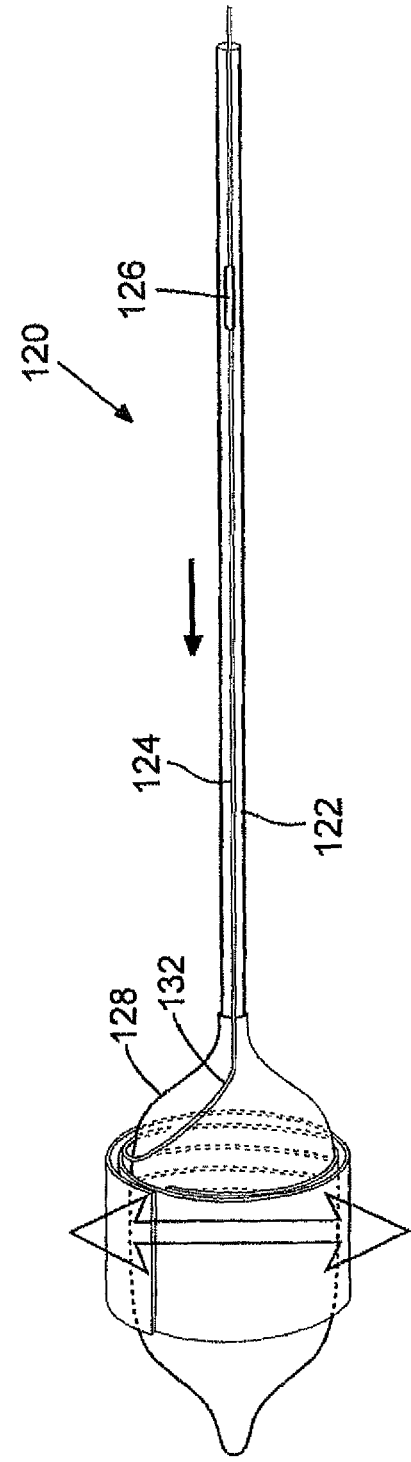

METHODS OF MEASURING HEART VALVE ANNULUSES FOR VALVE REPLACEMENT

FIELD

The present application relates to a system for measuring orifices and passageways in the human body, including, for example, heart valve annuli.

BACKGROUND

The accurate measurement of orifices and passageways in the human body is important for the success of a variety of medical procedures. In particular, accurate measurement of the anatomy of the human body is often crucial for the successful implantation of prosthetic devices. For example, in selecting a prosthetic heart valve, it is preferable to select the largest size valve possible. A large effective valve orifice is preferable because it creates less resistance to forward flow and requires the heart to do less work.

Traditional sizing of a heart valve annulus is performed by placing a known diameter sizing apparatus into the annulus and observing the fit of the sizing apparatus. If the sizing apparatus appears to fit easily into the annulus, the sizing apparatus is retracted and a larger sizing apparatus is inserted. In some procedures, the native annulus is expanded from its natural state due to the radial outward pressure of a prosthetic valve implanted within the native annulus. Unfortunately, known sizing apparatuses do not take into consideration the final, functional size of the annulus when expanded by the prosthetic valve. That is, these techniques cannot measure the size of a heart valve annulus when it is expanded under pressure.

SUMMARY

In one embodiment, an apparatus is provided for measuring an expanded internal orifice of a patient. The apparatus can comprise an orifice-expanding device, a pressure-measuring device, and a size-measuring device. The orifice-expanding device can be located at or near a distal end of the apparatus. The orifice-expanding device can be radially expandable from a first configuration to a second, expanded configuration to cause corresponding radial expansion of the orifice. The pressure-measuring device can be configured to measure a pressure applied to the orifice by the orifice-expanding device. The size-measuring device can allow a user to measure a dimension of the orifice after it has been expanded by the orifice-expanding device. The measurement of the dimension can be obtained independently of the pressure measurement measured by the pressure measuring device.

In specific implementations, the size-measuring device can comprise a coiled member. The coiled member can surround at least a portion of the orifice-expanding device and can be configured to uncoil when the orifice-expanding device expands from the first configuration to the second configuration.

In specific implementations, the coiled member can have an outer face with visual indicia that correspond to different dimensions for measuring the size of the expanded orifice. In other specific implementations, the coiled member can have a first end and a second end, with the first end being attached to a portion of the orifice-expanding device. The position of the second end of the coiled member relative to the outer face of the coiled member can identify the dimension of the expanded orifice.

In specific implementations, a shaft member can be connected to the orifice-expanding device and the size-measuring device can comprise a wire member that surrounds at least a portion of the orifice-expanding device. The wire member can have a first end and a second end, with the first end being fixed in position relative to the orifice-expanding device and the second end having a marker that is free to move longitudinally along the shaft. The position of the marker along the shaft can identify the dimension of the expanded orifice. In other specific implementations, the wire member can pass through openings in one or more bar members that are attached to the orifice-expanding device.

In specific implementations, the size-measuring device can comprise a locking member. The locking member can surround at least a portion of the orifice-expanding device, and can be configured to increase in diameter from a first position to a plurality of second positions. When the locking member is expanded to one of the plurality of second positions, the locking member can lock in that position, thereby preventing the locking member from returning to the first position. In other specific implementations, the locking member can be a one-way locking member that permits an increase in radial size of the size measuring member but prevents a decrease in radial size of the size measuring member.

In specific implementations, the orifice-expanding device can be an inflatable balloon. In other specific implementations, the pressure-measuring device can measure the pressure exerted by the balloon based on the volume of fluid added to the balloon.

In specific implementations, the orifice-expanding device can have one or more linkages that effect radial expansion of the orifice-expanding device, and the pressure-measuring device can comprise one or more strain gauges positioned on the orifice-expanding device.

In another embodiment, a method can comprise accessing an internal orifice of a patient's body, placing an orifice-expanding device of a sizing apparatus into the orifice, expanding the orifice-expanding device to cause it to exert a desired pressure against the orifice to cause the orifice to expand, and measuring a dimension of the expanded orifice independently of the pressure exerted by the orifice-expanding device.

In specific implementations, the orifice can comprise an annulus of a heart valve and the method further comprises selecting a prosthetic heart valve based on the measured dimension of the annulus, and implanting the heart valve in the annulus. In other specific implementations, the act of measuring a dimension of the expanded orifice can be accomplished while the orifice-expanding device is in the expanded orifice. In other specific implementations, the act of measuring a dimension of the expanded orifice can comprise reading visual indicia on the sizing apparatus and recording the measured dimension.

In other specific implementations, the sizing apparatus can comprise a coiled member surrounding at least a portion of the orifice-expanding device and which can uncoil upon expansion of the orifice-expanding device. The coiled member can have a first end and a second end, and the first end can be fixed relative to the orifice-expanding device. The coiled member can have visual indicia on a surface of the coiled member. The act of measuring a dimension of the expanded orifice can comprise observing the position of the second end of the coiled member relative to the visual indicia.

In other specific implementations, the sizing apparatus can comprise an elongated shaft and a movable indicator coupled to the orifice-expanding device and operable to move longitudinally of the shaft upon expansion of the orifice-expanding device. The act of measuring a dimension of the expanded orifice can comprise observing the position of the movable indicator relative to a location on the shaft.

In specific implementations, the act of measuring a dimension of the expanded orifice can be accomplished after the orifice-expanding device is removed from the body. In other specific implementations, the method can further comprise retaining the orifice-expanding device in an expanding state after the act of expanding the orifice-expanding device and removing the orifice-expanding device from the body in its expanded state in order to measure the dimension of the expanded orifice.

In specific implementations, the method can further comprise measuring the pressure exerted by the orifice-expanding device. In other specific implementations, the orifice-expanding device can be a balloon and the act of expanding can comprise inflating the balloon to expand the orifice. In other specific implementations, the orifice-expanding device can comprise one or more strain gauges and the method can further comprise measuring the strain on the orifice-expanding device when it is expanded and determining the pressure exerted against the orifice by the orifice-expanding device from the measured strain. In other specific implementations, the orifice-expanding device can comprise a non-cylindrical outer surface that generally corresponds to the shape of the orifice.

In another embodiment, a method can comprise radially expanding an orifice in a patient's body and indicating a dimension of the expanded orifice. The act of indicating the dimension of the expanded orifice does not include calculating the dimension based on the pressure exerted by the orifice-expanding device against the orifice.

In specific implementations, the orifice can comprise an annulus of a heart valve and the method can further comprise selecting a prosthetic heart valve based on the dimension of the annulus, and implanting the heart valve in the annulus.

In specific implementations, the act of radially expanding the orifice can comprise inserting an orifice-expanding device in the heart valve annulus and expanding the orifice-expanding device to expand the annulus. The method can further comprise measuring the pressure exerted by the orifice-expanding device against the annulus in order to expand the annulus to a desired pressure.

In specific implementations, the act of radially expanding the orifice can comprise inserting an orifice-expanding device in the heart valve annulus and expanding the orifice-expanding device to expand the annulus. The act of indicating can comprise indicating the diameter of the expanded annulus after it is expanded by the orifice expanding device, and the act of implanting the heart valve can comprise inserting the heart valve in the annulus and expanding the heart valve to expand the annulus and anchor the heart valve in the expanded annulus. The diameter of the expanded annulus after implanting the heart valve can be approximately the same as the diameter of the annulus after it was expanded by the orifice-expanding device.

In specific implementations, the act of implanting the heart valve can comprise inserting the heart valve in the annulus and expanding the heart valve to expand the annulus and anchor the heart valve in the expanded annulus. The pressure exerted by the expanded heart valve can be approximately the same as the desired pressure.

In another embodiment, an apparatus for measuring a heart valve annulus of a patient is disclosed. The apparatus can comprise expansion means for expanding the heart valve annulus and measuring means for measuring the diameter of the expanded annulus. In other specific embodiments, the apparatus can further comprise means for measuring the pressure exerted by the expansion means against the annulus to allow expansion of the annulus to a desired pressure.

The foregoing and other objects, features, and advantages of the invention will become more apparent from the following detailed description, which proceeds with reference to the accompanying figures.

BRIEF DESCRIPTION OF THE DRAWINGS

FIG. 2 is a perspective view of a device for sizing an orifice, with the device shown in an unexpanded configuration, according to one embodiment.

FIG. 3 is an end view of the device of FIG. 2.

FIG. 4 is a view of the device of FIG. 2, with the device shown in an expanded configuration.

FIG. 5 is an end view of the device of FIG. 4.

FIG. 17 is a side view of a portion of a device for sizing an orifice, according to another embodiment.

FIG. 18 is a side view of a portion of a device for sizing an orifice, according to another embodiment.

DETAILED DESCRIPTION

Figure 1A:
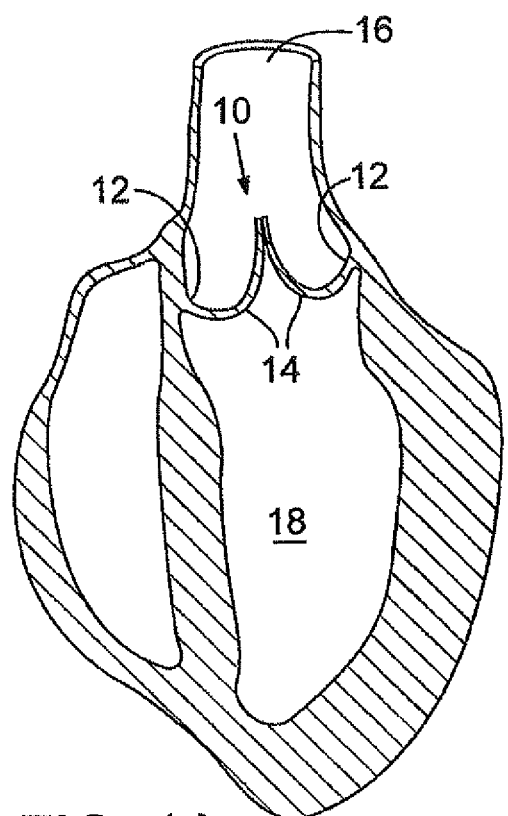
FIG. 1A is a cross-sectional view of an illustration of a portion of a human heart with the aortic leaflets in the closed position.

It is often useful to obtain a size measurement of a human orifice. Such sizing is particularly useful during or prior to implantation of prosthetic devices where it can be desirable to obtain a tight fit between the prosthetic device and the orifice into which the prosthetic device will be positioned. Traditionally, such sizing is performed without any consideration of the pressures that the prosthetic device may exert on the orifice during the implantation procedure or orifice dimensional changes due to various physiological conditions (e.g., systolic and diastolic pressures). If the prosthetic device is to be placed into the orifice and then expanded to achieve a tight fit between the prosthetic device and the orifice, the size of the orifice will expand during such a procedure and such expansion should be taken into consideration when sizing the orifice. Thus, it is desirable to either measure the size of the orifice at (1) pressures similar to, or somewhat less than, that which will be applied during implantation of the prosthetic device or (2) pressures that mimic actual targeted physiological conditions to establish a baseline for bio-prosthesis sizing. As used herein, the term "orifice" means any body orifice, annulus, or lumen within the body.

The aortic valve annulus is an example of an orifice that requires accurate sizing for the implantation of a prosthetic device. Surgically implanted heart valves are traditionally sized so that they are small enough to fit into the anatomical location, yet still large enough to fill the space when they are sewn to the patient's annulus. In some circumstances, it may be desirable to secure the valve with an expandable outer stent that exerts a radial outward force on the tissue of the annulus. The outward force exerted by the expanding stent can desirably enlarge the annulus, which allows a surgeon to implant a larger valve in a patient. A larger valve is generally desirable because it creates less resistance to forward flow and requires the heart to do less work.

By inserting a stent that expands the annulus, it is also possible to reduce or eliminate paravalvular leaks by forcing the elastic tissue in the annulus to conform to the more rigid stent. In addition, the outward radial force provided by the stent is directly proportional to the frictional resistance to axial movement. Thus, by increasing the size of the valve, paravalvular leaks can be reduced or eliminated and the axial stability of the device can be improved.

With anatomical structures that have highly variable non-linear elastic modulus that vary significantly from patient to patient, the sizing of the orifice when expanded under pressure can be particularly important. In such cases, the actual normal force that is critical to the frictional resistance to axial movement of the valve for a particular patient cannot be easily determined. To assure the selection of a valve that will provide adequate frictional resistance, a sizing apparatus in particular embodiments can be used to expand an orifice by an application of a radial force similar to, or somewhat less than, the force that will be applied to the surrounding tissue by the deployed prosthetic device. The sizing apparatus desirably includes an orifice-expanding device that allows a surgeon to apply a desired level of force to expand the native orifice, and a measuring device that allows the surgeon to measure the size (e.g., diameter) of the expanded orifice at the desired level of force.

In particular embodiments, a sizing apparatus is provided that allows a surgeon to view the sizing apparatus and the orifice to be sized during the sizing procedure. By providing a sizing device that is capable of being visually observed during expansion of an orifice, it is possible to visually ensure that the device is located in the area of the anatomy that the user intends to measure. The sizing apparatus can also include a measuring device having visual indicia that allows the surgeon to measure the size of the expanded orifice while the distal end portion of the apparatus is still in the expanded orifice.

Figure 1B:
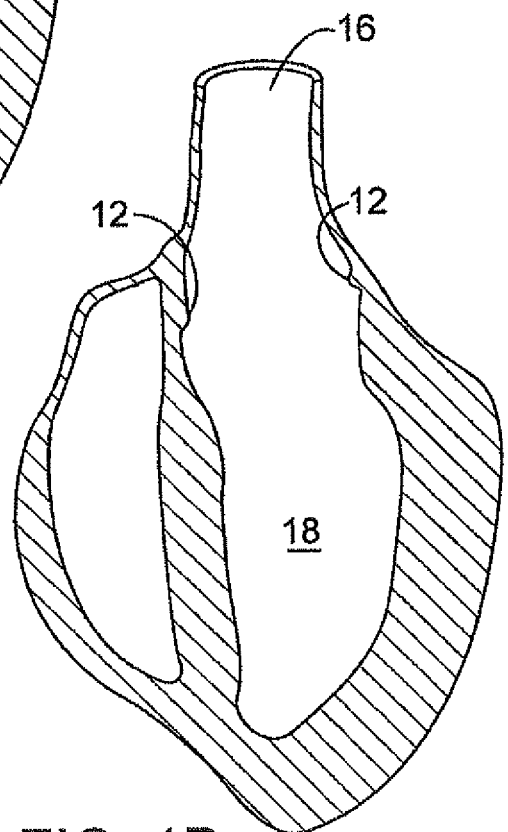
FIG. 1B is a cross-sectional view of an illustration of a portion of a human heart with the aortic leaflets removed.

Embodiments of a sizing apparatus that can be used, for example, to size an aortic valve annulus are discussed in greater detail below. FIG. 1A is a cross-sectional view of an illustration of a portion of a human heart. Native aortic valve 10 includes valve annulus 12 and native leaflets 14. Aortic valve 10 is located between the aorta 16 and the left ventricle 18. FIG. 1B is another cross-sectional view of the human heart. FIG. 1B is similar to FIG. 1A, but with the native leaflets removed in preparation of receiving a prosthetic heart valve, such as a surgically implanted heart valve. Although the figures shown here depict the sizing of orifices with various native structures removed (e.g., the aortic valve leaflets), the device for sizing orifices disclosed herein can also be used, if desired, to measure orifices with such native or artificial structures intact. The sizing apparatus can also be adapted to measure the size of other orifices or lumens within the body.

FIGS. 2 and 3 show views of an embodiment of a sizing apparatus 20 in an unexpanded configuration. Sizing apparatus 20 includes a handle portion 22, fluid passageway, or fluid conduit, 24, shaft 26, balloon 28, and coil member 30. Handle portion 22 and shaft 26 are desirably curved and/or malleable (flexible) to facilitate use of sizing apparatus 20 and to provide improved access of the sizing apparatus 20 into the lower portion of the aorta. Handle 22 also desirably has a grip surface, which provides a more comfortable and stable surface for the surgeon to hold onto during a sizing procedure. Shaft 26 passes through handle portion 22 and is in fluid connection with fluid passageway 24. Alternatively, shaft 26 can contain another internal conduit that is in fluid connection with fluid passageway 24.

Balloon 28 is attached to the distal end of shaft 26. Fluid passageway 24 and shaft 26 deliver to the balloon 28 a fluid that is capable of inflating balloon 28. Coil member 30 can be a thin sleeve of a flexible material that is relatively non-elastic. For example, a thin sleeve of a non-elastic plastic film can be coiled around balloon 28. Desirably, the coiled member is formed of a non-elastic material so that as it unwinds it is relatively uniform and constant in length. Coil member 30 can be formed of any suitable material, including, for example, plastics, non-elastic films, metals, or the like.

FIG. 3 is a bottom view of sizing apparatus 20. As seen in FIG. 3, the size-measuring device of this embodiment comprises a coil member 30 is wrapped around (or coiled around) balloon 28. Coil member 30 has two ends. Coil member 30 is desirably attached to balloon 28 at the first end 32. The first end can be attached to the balloon by any known attachment methods, such as gluing, bonding, welding, stitching, or other mechanical fasteners. The second end 34 of coil member 30 is located on the outside of the coil member. Coil member 30 is desirably formed so that it is pre-stressed in a tightly wound coil, with second end 34 pressed firmly against the outer surface of coil member 30.

FIGS. 4 and 5 show views of sizing apparatus 20 in an expanded condition. To expand coil member 30, fluid from a fluid pressurizing device (such as the device shown in FIG. 7) passes through fluid passageway 24, through the handle portion 22, through shaft 26, and into balloon 28. As balloon 28 expands, coil member 30 uncoils, and second end 34 changes position on the outside of coil member 30. That is, as balloon 28 expands, second end 34 recedes, or moves back, from its unexpanded position and more of the outer surface of coil member 30 is exposed.

Figure 6:
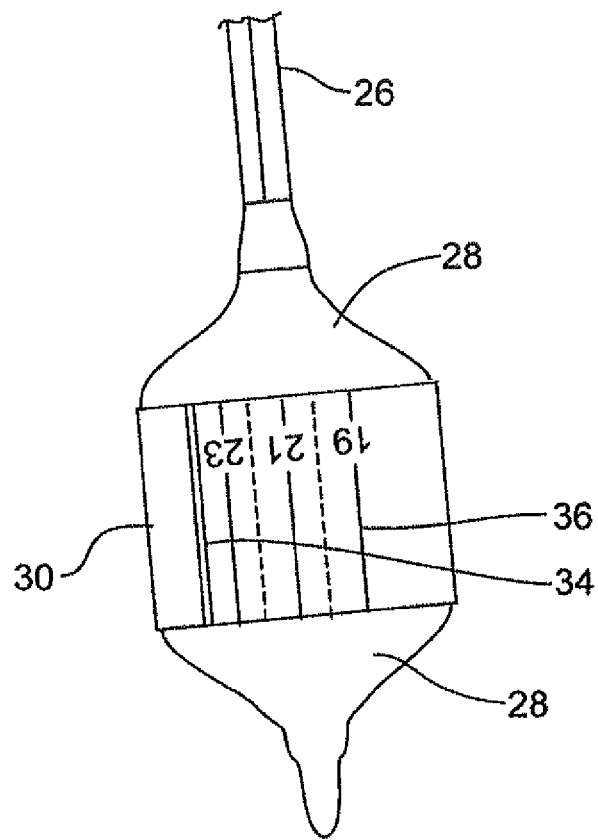
FIG. 6 is a partial view of a device for sizing an orifice with visual indicia used for measuring the size of the orifice.

As shown in FIG. 6, sizing apparatus 20 can include pre-marked visual indicia, such as indicator lines 36, for measuring a dimension (e.g., the diameter) of the expanded native orifice. The indicator lines 36 can include solid lines indicating a first set of sizes, e.g., 19 mm, 21 mm, and 23 mm, and dotted lines indicating a second set of sizes, e.g., 20 mm and 22 mm. The indicator lines 36 are positioned so that they align with the second end of coil member 30 when the expandable member is in its expanded condition. The indicator lines and other related visual indicia can be printed on the outside of coil member 30 so that it is visible to the operating surgeon during the sizing procedure. In this manner, the diameter of the expanded coil member 30, and therefore the expanded orifice, can be visually determined by observing where second end 34 meets the indicator lines on the outside of coil member 30.

Figure 7:
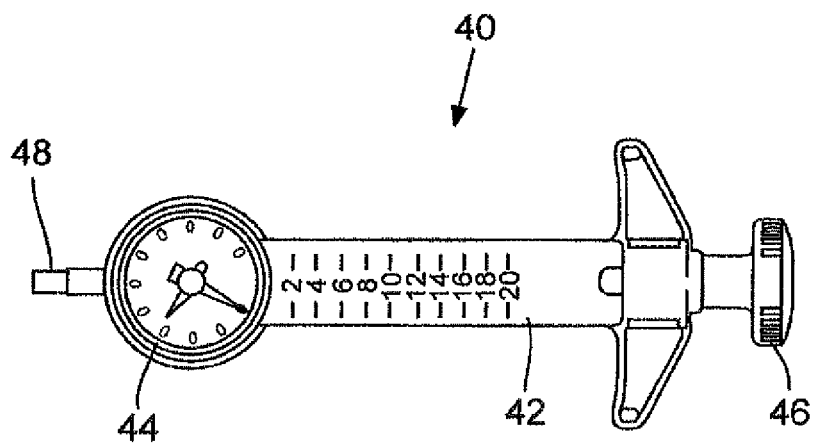
FIG. 7 is a fluid pressurization device for use with a sizing device that has an expandable balloon member.

Balloon 28 can be expanded using any known fluid pressurizing device that is capable of expanding balloon catheters to known pressures. For example, FIG. 7 illustrates a known inflation device such as is described in U.S. Pat. No. 5,713,242, which is incorporated by reference herein. As described in more detail in U.S. Pat. No. 5,713,242, fluid pressurization devices utilize known volumes of fluid to inflate balloon catheters to various measured pressures. Referring to FIG. 7, fluid pressurization device (or inflator device) 40 comprises a cylindrical syringe body and fluid displacement chamber 42, a pressure monitoring gauge 44, and a knob 46. Knob 46 is turned to actuate an internal threaded plunger that causes fluid to leave the fluid displacement chamber 42 and exit fluid pressurization device at connector 48. Connector 48 is fluidly connected to fluid passageway 24 of the sizing apparatus (shown, for example, in FIGS. 2, 4, and 6). Accordingly, as knob 46 is adjusted, fluid flows from fluid pressurization device 40, through the sizing apparatus, and into balloon 28. Using a fluid pressurizing device such as that disclosed in U.S. Pat. No. 5,713,242, the balloon can be inflated to a known pressure. Alternatively, a pressure relief valve can be employed to make sure the correct pressure is used, which can eliminate the need for a pressure gauge.

Figure 8:
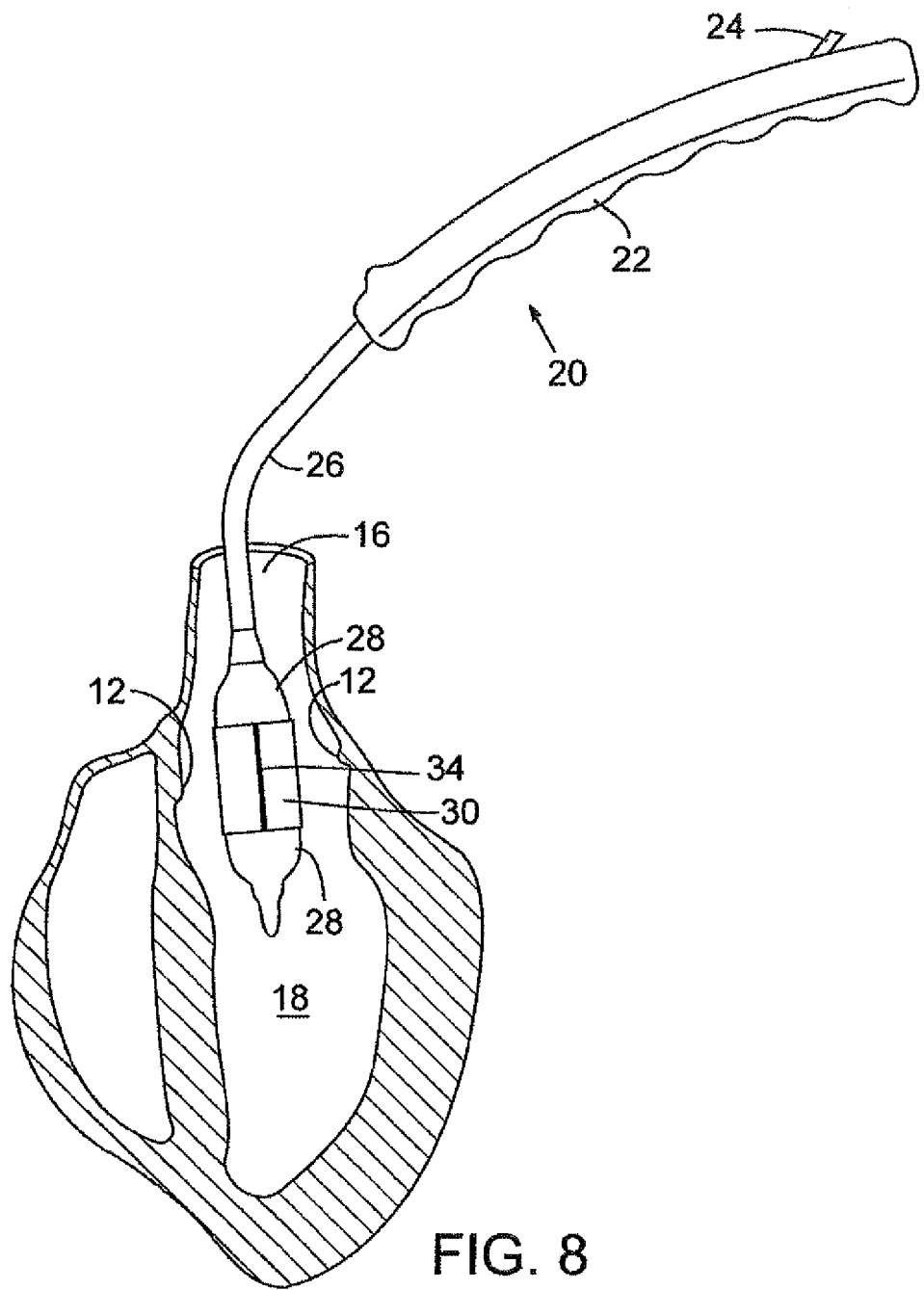
FIG. 8 is a cross-sectional view of an illustration of a portion of a human heart shown with a device for sizing an orifice positioned near an aortic valve.
Figure 9:
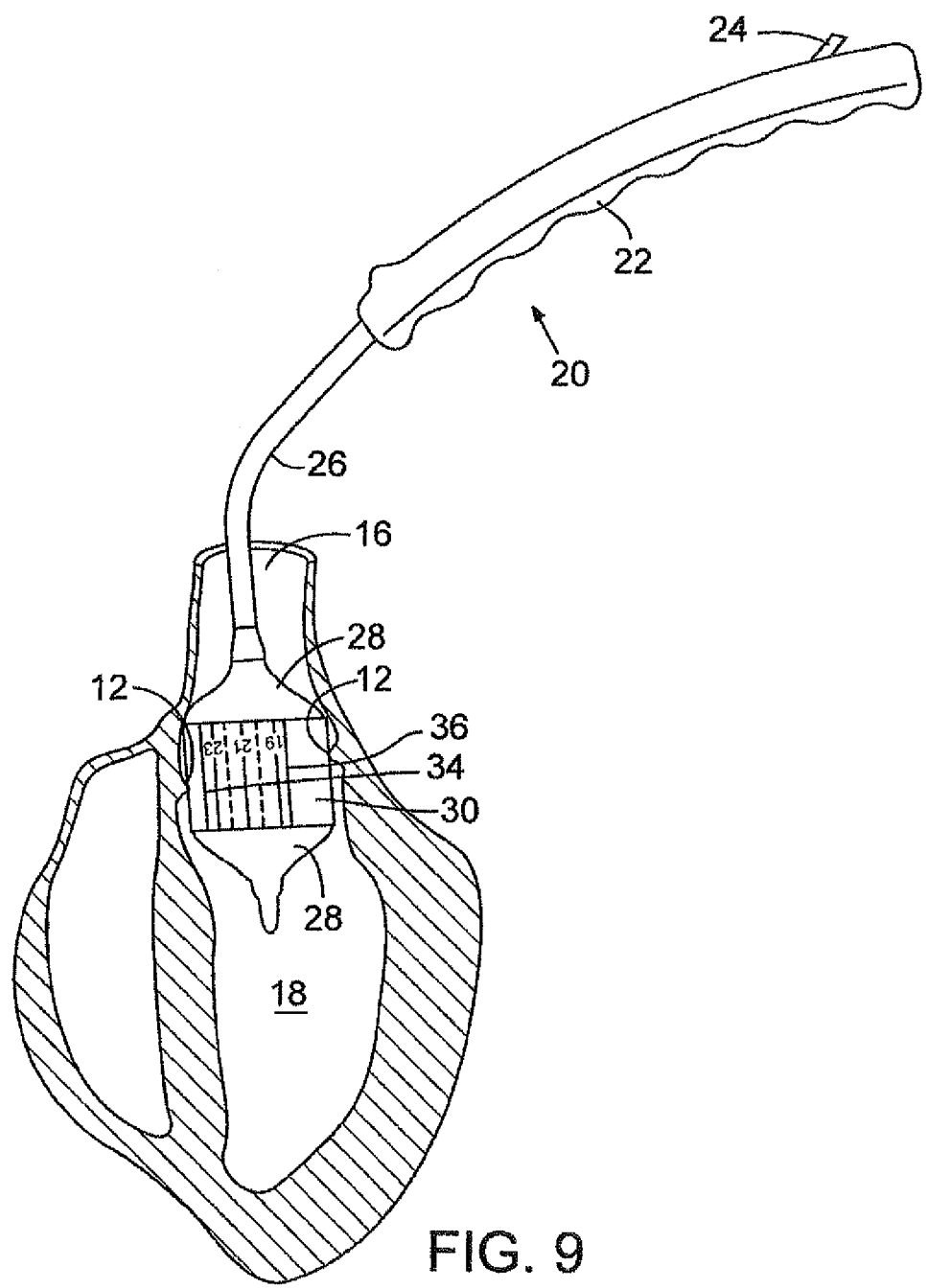
FIG. 9 is a cross-sectional view of an illustration of a portion of a human heart shown with the device of FIG. 8 in an expanded configuration.

FIG. 8 shows an illustration of sizing apparatus 20 being used to size the aortic valve annulus 12 of a human heart. Access to the heart can be achieved by any known surgical technique. For example, access to the aortic valve can be achieved by an upper mini-sternotomy. After gaining access to the aorta, the balloon 28 of the sizing apparatus 20 can be inserted into the space of the aortic valve annulus 12. Using handle portion 22, the sizing apparatus can be maneuvered until it is positioned in the appropriate location for expansion and measurement of the valve annulus. A fluid pressurization device (such as described above) can be connected to fluid passageway 24 and fluid can be sent through the sizing apparatus to expand balloon 28. Balloon 28 is preferably expanded to a pressure greater than 120 mm Hg, and more preferably to a pressure greater than 250 mm Hg.

For certain applications, an implantable, radially-expandable valve may be expanded by a balloon inflated to about 3800 mm Hg (5 atmospheres). Accordingly, it may be desirable to expand the sizing apparatus to a pressure that approximates the pressure the valve annulus will experience during expansion of the valve. In order to approximate the pressure that the annulus will experience under valve expansion, it is desirable to apply the same pressure or less pressure than the annulus will experience under valve expansion. Thus, it may be desirable to expand balloon 28 to a pressure between about 200 mm Hg and 5320 mm Hg (7 atmospheres,) and more desirably between about 250 mm Hg and 500 mm Hg.

Alternatively, it can be desirable to measure the maximum diameter achieved by the valve annulus during the cardiac cycle, which occurs at the end of systole for the aortic valve. This measurement can then used to establish a baseline for selecting the size of the bio-prosthesis. To determine the maximum diameter of the valve annulus, the sizing apparatus can be pressurized (or expanded) to mimic the physiological condition of the annulus at its greatest diameter. Thus, the pressure that is used to inflate (or expand) the sizing apparatus can be the pressure to actuate (open) the sizing apparatus plus approximately between about 250 mmHg and 500 mmHg, and more preferably about 350 mmHg. This pressure range provides a pressure on the valve annulus that is equal to an estimated maximum physiological pressure seen by the aortic valve annulus (approximately 140 mmHg) plus an additional amount to ensure that the measured size of the annulus corresponds to a valve size that will provide a proper interference fit with the annulus, thereby reducing the likelihood of implant migration and providing improved hemodynamic performance.

After balloon 28 is expanded to the desired pressure, a reading can be obtained from the indicator lines 36 of the sizing apparatus 20. Specifically, the indicator line that aligns with second end 34 of coil member 30 identifies the size of the expanded coil member 30, which corresponds to the size of the expanded orifice. For example, if balloon 28 is expanded and second end 34 of coil member 30 aligns with an indicator line that corresponds to a diameter of 22 mm, the expanded diameter of the orifice can be determined to be 22 mm.

In this embodiment and in other embodiments discussed below, a surgeon can use a pressure measurement or other pressure indicator as a means for determining how much the apparatus will be (or should be) expanded within the orifice. The measurement of the orifice size, however, can be determined independent of the pressure applied. For example, the size measuring device 30 does not attempt calculate the size of an orifice by translating balloon pressure into a balloon diameter; rather, the size measurement device performs the measurement of the orifice independent of the pressure applied, thereby providing a more accurate measurement of the orifice.

As discussed above, desirably, the size of the expanded orifice can be visually determined in-situ by a surgeon by viewing the position of the second end 34 of coil member 30. By providing visual access to the expanded orifice, in addition to knowing the amount of pressure applied to the orifice (as discussed above), the surgeon can visually determine the condition of the expanded orifice. For many applications, the elasticity of a particular orifice can vary greatly between patients and, therefore, it is desirable, if not necessary, to be able to determine the effect of the expandable member on the patient's orifice. This can be particularly true with orifices that are calcified or otherwise diseased. Variations in state of disease, as well as variations in natural elasticity, can make it difficult to approximate the amount of expansion desired in a particular application without first applying a force similar to the force applied by the device subsequently implanted in the annulus and then directly viewing the treatment site for changes prior to implanting the prosthetic device in the annulus.

If the access to the heart and anatomy of the patient permits it, a surgeon could also remove the sizing apparatus from the body, in the expanded form and obtain the size of the expanded coil member in that manner. Alternatively, if a view of the coil member is obstructed by the anatomy of the patient, a surgeon could use other view enhancing equipment to obtain the size of the expanded coil member. For example, a surgeon could use a videoscope to see the markings on the coil member more clearly.

Other markings techniques could be implemented that permit the surgeon to deflate the balloon, remove the sizing apparatus from the body, and then determine the size of the earlier expanded coil member. For example, the coil member could be configured such that the second end of the coil member leaves a visible or otherwise observable mark at its largest expanded location. A surgeon could then view this mark once the sizing apparatus is removed from the body and the expanded size of the sizing apparatus could be determined in this manner.

Figures 10, 11:
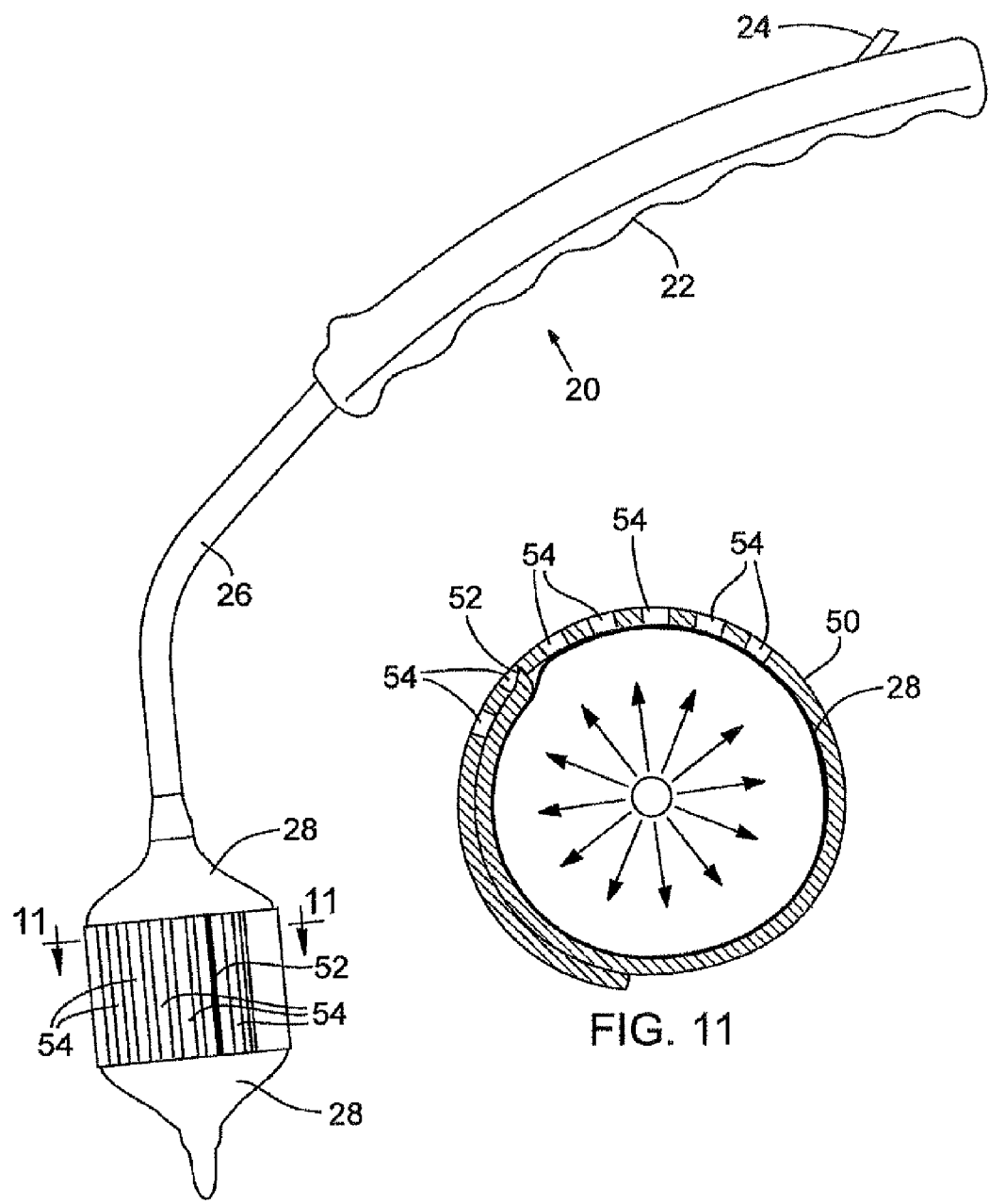
FIG. 10 is a side view of a device for sizing an orifice, with the device shown in an expanded configuration.
FIG. 11 is an end view of the device of FIG. 10.

FIGS. 10 and 11 illustrate another embodiment of a sizing apparatus with a coil member 50. Coil member 50 includes a ratcheting-type locking mechanism 52. The locking mechanism 52 in the illustrated embodiment comprises a radially protruding ramp-like member that extends into spaces 54 in coil member 50. As balloon 28 expands, coil member 50 expands and locking mechanism 52 locks coil member in the expanded position. Thus, spaces 54 provide locking mechanism 52 with a plurality of positions in which it can lock. The locking mechanism in the illustrated embodiment is a one-way locking mechanism. Accordingly, although coil member 50 can enlarge from a first position with a relatively small radial size, to a number of positions with a larger radial size (as defined by spaces 54), the locking mechanism 52 prevents coil member 50 from returning to the first position, or to other radially smaller positions once it has been enlarged.

Thus, when coil member 50 reaches its maximum expansion with the locking mechanism 52 extending into an aperture 54, locking mechanism 52 maintains coil member 50 in that position. Coil member 50 can include visual sizing indicia as discussed above. Alternatively, coil member 50 can be removed from the body and the size determined by some other measurement technique.

Figures 12, 13:
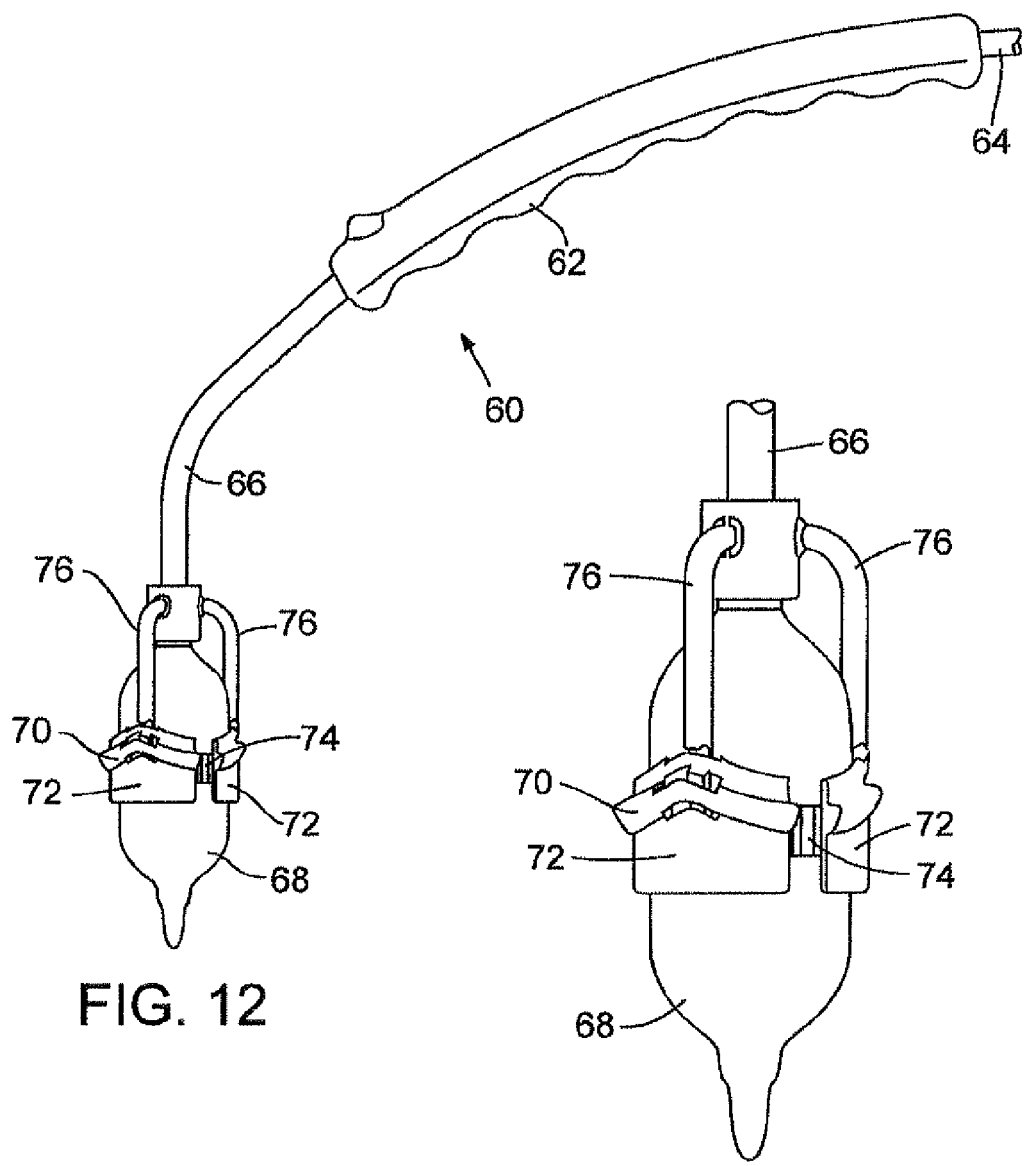
FIG. 12 is a side view of a device for sizing an orifice, according to another embodiment.
FIG. 13 is an enlarged view of the distal end portion of the device shown in FIG. 12.
Figure 14:
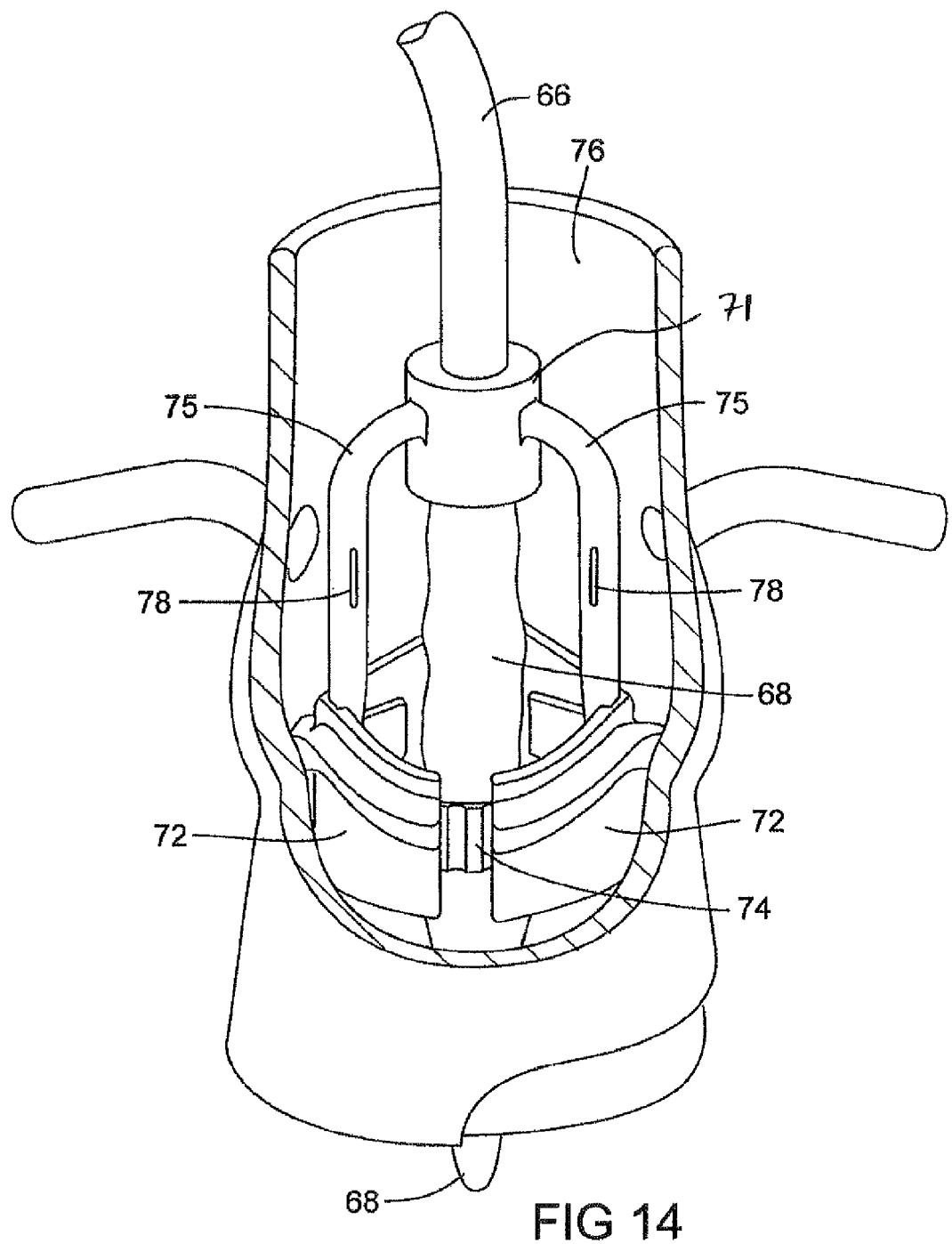
FIG. 14 is a partial cross-sectional perspective view of an illustration of a portion of an aorta shown with the device of FIG. 12 positioned near the aortic valve.

FIGS. 12-14 illustrate another embodiment of a sizing apparatus 60. Sizing apparatus 60 includes a handle portion 62, a fluid passageway 64, a shaft 66, and a balloon 68, each of which are similar to those elements discussed above with regard to the other embodiments. Sizing apparatus 60 also includes an expandable sizer 70. Expandable sizer 70 is desirably shaped so that it approximates the shape of the annulus that is to be measured. In this example, expandable sizer 70 is shaped in a tri-lobe configuration that approximates the shape of the aortic valve annulus.

The sizer 70 comprises a hub 71 mounted to the distal end of the shaft 66 adjacent to balloon 68, a plurality of elongated arms 76 (three in the illustrated embodiment) attached to and extending from the hub 71, and a plurality of expanding portions 72 (three in the illustrated embodiment) mounted to the distal end portions of the arms. The expanding portions 72 extend circumferentially about balloon 68 and have outer surfaces that desirably are shaped to generally conform to the tri-lobe shape of the aortic valve annulus. A locking mechanism 74 can be mounted on the inner surfaces of the expanding members 72.

As shown in FIG. 14, expandable sizer 70 of sizing apparatus 60 can be inserted into the aorta 76 to determine the size of the aortic valve annulus in an expanded condition. As balloon 68 expands, it exerts a radial force on the expanding portions 72 (only two are shown in FIGS. 12-14 for clarity). Expanding portions can be interconnected via locking mechanisms 74. Any number of arms can be used to secure the expanding portions 72 to the shaft 66; however, desirably, there are two or more arms. In addition, while three expanding portions 72 are used in the illustrated embodiment, a greater or fewer number of expanding portions can be used.

As seen in FIG. 14, locking mechanisms 74 can have grooves that lock the expandable sizer 70 in any of a plurality of expanded positions. In particular, the grooves (or teeth) shown in FIG. 14 mate with opposing grooves (or teeth) on the inside of expanding portions 72, permitting the expanding portions to move away from one another, while at the same time preventing them from collapsing back towards each other after the balloon 68 is deflated. FIG. 14 shows expanding sizer 70 after balloon 68 has been expanded and subsequently deflated. The grooves of the locking mechanisms 74 have effectively locked the expandable sizer 70 into an expanded position. Accordingly, a surgeon can then remove the sizing apparatus 60 from the patient's body and determine the size of the expanded orifice under the known pressure that was applied by balloon 68. The size of the expanded orifice can be determined by any measuring technique, including, for example, fitting the removed sizer into a secondary hole gauge to determine the size of the expanded portions. The secondary hole gauge could include various size openings and the surgeon can determine the size of the expanded portions by placing the sizer in the various openings until the proper size of the expanded portions is determined.

In addition, one or more strain gauges 78 can be positioned on one or more of arms 76. Strain gauges 78 can be electrically connected to a processor that can be housed in the handle. As can be seen, outward radial movement of expanding portions 72 causes corresponding outward deflection of the distal ends of arms 76, which in turn increases the strain on the arms. The processor measures the strain on arms 76 and calculates a value corresponding to the pressure or force applied to the valve annulus by the expanding portions 72 based on the measured strain. Strain gauges 78 can be any of a variety of commercially available strain gauge, such as, for example, metal foil type strain gauges. The strain gauge can be used in combination with the pressure monitoring gauge (discussed above) to determine the amount of pressure applied to the expanding portions 72, or it can be used independent of the pressure monitoring gauge. The sizing apparatus can include a visual alpha numeric display located on the handle or at another convenient location to display the pressure applied by the sizer against the annulus. The processor can be any type of processor that can receive electrical signals from the strain gauges and calculate a value corresponding to pressure or force.

Figure 15:
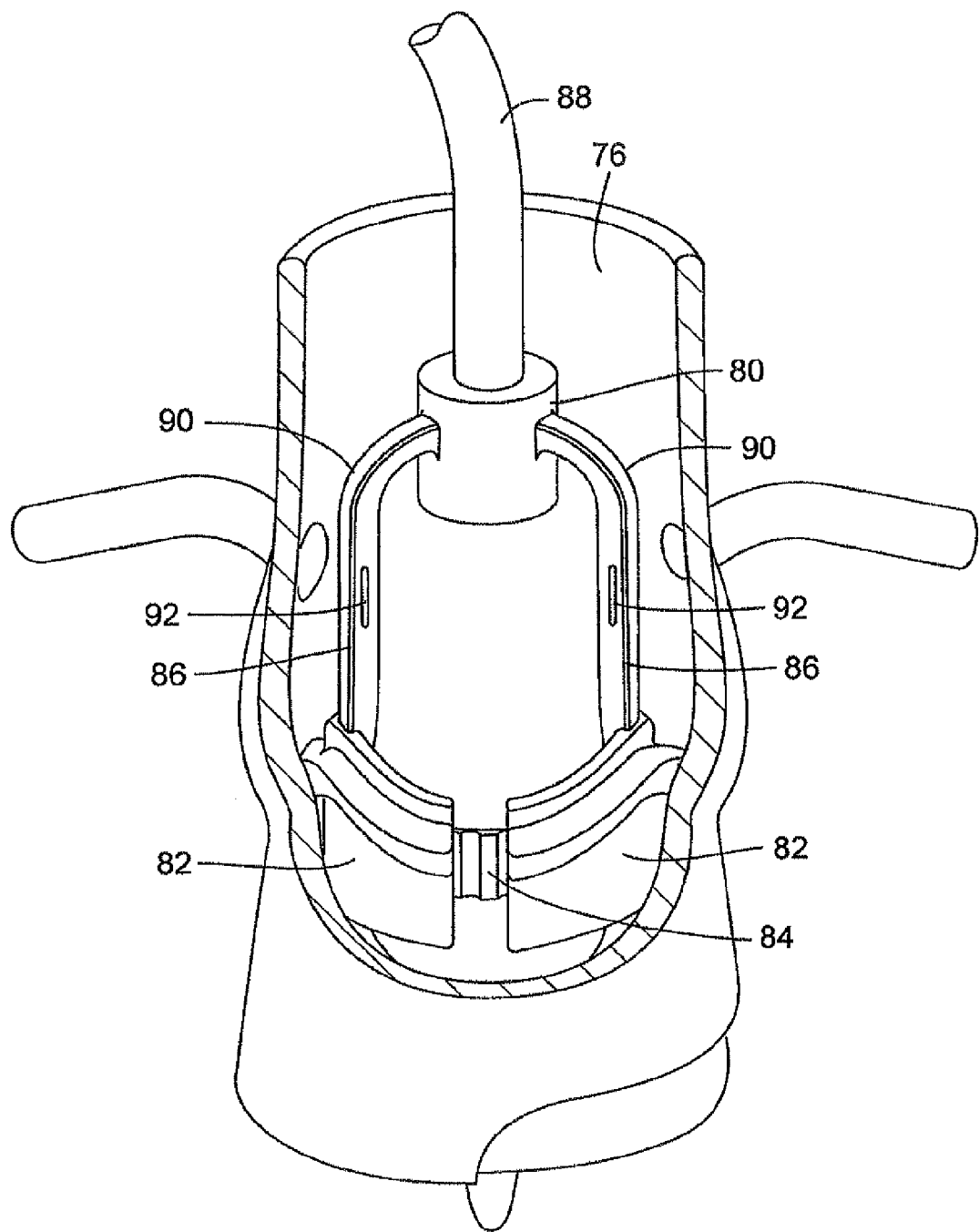
FIG. 15 is a partial cross-sectional perspective view of an illustration of an aorta shown with the device of FIG. 14 in an expanded position.

In another embodiment, the balloon can be omitted and the expanding sizer 70 can be mechanically expanded to the appropriate size within the annulus. Referring to FIG. 15, a mechanically expandable sizing apparatus 80, according to one embodiment, is disclosed. Expanding portions 82 can be interconnected to each other via locking mechanisms 84 as discussed above. However, instead of expanding the expanding portions using a balloon, expanding portions can be mechanically expanded. For example, pull wires 86 can extend through arms 90 and through shaft 88 to a handle (not shown). The pull wires 86 can be attached to the handle, which can include any number of mechanical mechanisms for applying pressure to pull wires 86. For example, the handle can have a rotatable knob coupled to the pull wires to increase and decrease tension on the pull wires by rotation of the knob. The application of tension on pull wires 86 causes the expanding portions 82 to expand radially outwardly from one another. Since there is no known fluid expansion to determine the amount of pressure that is being applied to the sizing apparatus, one or more strain gauges 92 can be positioned on arms 90. Strain gauges 92 can be electrically connected to a processor that can receive signals from the strain gauges and calculate a value corresponding to the pressure applied by the expanding portions 82 against the surrounding tissue, as described above. Rather than pull wires, any number of known mechanical techniques can be used to mechanically expand the sizing apparatus.

Figure 16:
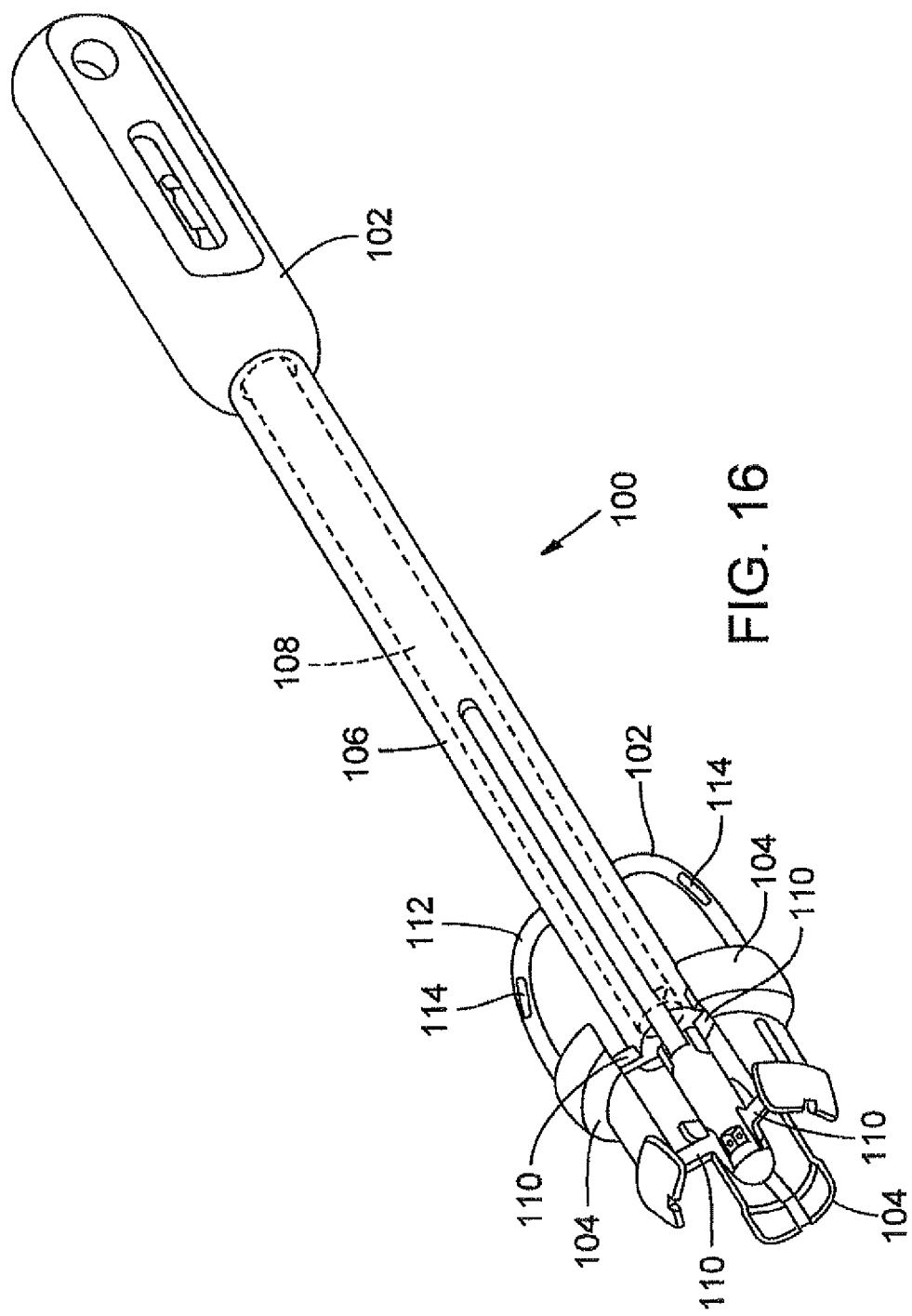
FIG. 16 is a perspective view of a device for sizing an orifice, according to another embodiment.

For example, as shown in FIG. 16, various linkages can be used to cause radial expansion of the expanding portions of a sizing apparatus. Mechanical expanding sizer 100 comprises a handle portion 102, expanding portions 104, and a shaft 106. An internal extension member 108 extends longitudinally inside of shaft 106 from the handle portion 102 to linkages 110. Linkages 110 are connected to expanding portions 104 such that upon longitudinal movement of extension member 108 toward handle portion 102, the linkages are forced radially outward, thereby increasing the perimeter size of the expanding portions 104. Arms 112 connect expanding portions 104 to shaft 106. Strain gauges 114 can be attached to arms 112 and electrically connected to a processor that can be stored in handle portion 102. By obtaining strain measurements of arms 112, the amount of pressure applied by expanding portions 104 to surrounding tissue can be determined. After expanding an orifice at a desired pressure by expansion of expanding portions 104, the sizer 100 can be removed from the orifice and the size of the orifice (as determined by the expanding portions 104) can be measured. Desirably, after the orifice is expanded, the extension member 108 can be secured in place, thereby maintaining the position of the expanding portions 104 while the sizer 100 is removed from the orifice. Thus, expanding portions 104 can be expanded to apply a known pressure to the orifice and a measurement of a dimension (e.g., diameter) of the expanded orifice can be determined.

Expanding portions of a mechanical expanding sizer can be cylindrical or non-cylindrical. As shown in FIG. 16, expanding portions 104 can be configured to have a shape that generally corresponds to the shape of the orifice to be measured. For example, expanding portions 104 can have a tri-lobe configuration that corresponds with the shape of an aortic valve annulus, as shown in FIG. 16. The non-cylindrical shape can further be extended to the other embodiments discussed above, and need not be limited to the mechanical expanding sizer shown in FIG. 16. For example, a non-cylindrical shaped balloon member can be used as the expandable member. Alternatively, a sizing apparatus can compromise a size-measuring device having a non-cylindrical outer surface. The size-measuring device can be disposed around a cylindrical balloon, which is inflatable to cause the non-cylindrical size measuring device to expand.

In another embodiment, an indicator can be provided on a portion of the sizing apparatus other than the orifice-expanding device, such as the shaft or the handle, so that the size of the expanded orifice can be readily determined by a surgeon while the sizing apparatus is still in the body without requiring direct visual access to the portion of the sizing apparatus within or near the orifice. FIG. 17 shows an embodiment that permits a surgeon to measure an orifice without direct visual access to the portion of the apparatus that is placed in the body. As shown in FIG. 17, a sizing apparatus 120 comprises a handle portion (not shown, but similar to those discussed above), a shaft 122 with a lumen 124 passing through shaft 122, and a balloon 128 fitted on the end of shaft 122. Balloon 128 is in fluid connection with a fluid passageway (as discussed above) so that the balloon 128 can be expanded to size an orifice.

A tag indicator 126 can be disposed on an outside surface of shaft 122. Alternatively, tag indicator 126 can be disposed inside (or partially inside) shaft 122 with a window member making the indicator visible from outside of shaft 122. A wire 132 is connected to tag indicator 126 and passes through the lumen 124 of shaft 122. Wire 132 then passes through openings on bars 130, which can be mounted on the outer surface of balloon 128 at regular intervals around balloon 128, and forms a coil extending around the balloon. A distal end of the wire 132 is secured to one of the bars 130. When balloon 128 is expanded, the coil of wire 132 that wraps around balloon 128 is increased and the tag indicator 126 is pulled closer to balloon 128, as shown by the arrows of FIG. 17. Thus, the outer diameter (or size) of balloon 128 can be determined by the location of tag indicator 126 along the shaft 122. Desirably, shaft 122 includes visual indicia (or graduations) so that the size of the expanded balloon 128 can be determined by observing the location of tag indicator 126 with reference to the indicia on shaft 122. The visual indicia desirably are provided along a section of the shaft that allows the surgeon to observe the position of the indicator 126 relative to the visual indicia while the expanded balloon is still within the orifice.

FIG. 18 is another embodiment of a sizing apparatus 120 that includes a wire 132 that is connected to a tag indicator 126 to determine the expanded size of the balloon 128. The embodiment of FIG. 18 is similar to that of FIG. 17, except that wire 132 is attached to a coil member 134 rather than to bars 130. The coil member 134 can comprise a non-elastic, flexible piece of material, similar to coil member 30 shown in FIGS. 2-5. As shown in FIG. 18, the wire 132 is wound around the balloon to form a wire coil and the coil member 134 is wound over the wire coil with a distal end of the wire secured to the inner surface of the coil member 134. As the coil member 134 and the wire coil expand with the balloon 128, tag indicator 126 is pulled towards the balloon 128, as shown by the arrows in FIG. 18. Thus, just as above, the tag indicator 126 can be used to determine the size of the expanded balloon 128, which also corresponds to the size of the orifice under the pressure applied by the expanded balloon.

As discussed above, sizing determinations can be made visually by the implanting surgeon. That is, the implanting surgeon can observe markings on the expanding device in-situ and determine the size of the expanded annulus. Alternatively, the implanting surgeon can remove the expanded device from the patient and either visually determine the appropriate size based on markings on the device or measure the expanded device in some other manner (such as, for example, by fitting the expanded device into pre-sized hole gauges as discussed above). In either case, however, it is desirable that the surgeon be able to visually observe the expanded orifice to make a determination as to whether the orifice is sufficiently expanded.

Sizing can also be achieved without visually observing the sizing apparatus, such as by taking readings off a tag indicator or from a strain gauge as discussed above. Alternatively, sizing can be determined by radiography or echocardiography. This would be especially useful for a sizing apparatus that is deployed via a catheter and that must be deflated or contracted before removal from the body can be achieved.

When implanting valves, surgeons often find that the first selected valve is too small and that the patient would benefit from upsizing to a larger valve. By using the sizing apparatus and method described above, an implanting surgeon can determine the valve size that will be appropriate when the annulus is expanded. Accordingly, the surgeon will not have to experiment with various smaller size valves before finding the valve that is most appropriate to the particular size annulus. Moreover, not only can the surgeon determine the size of the valve that will properly fill the annulus, but the surgeon can determine the size of the valve that will be large enough to exert sufficient frictional resistance to axial movement.

Any standard heart valve surgery techniques can be used to gain access to the heart to obtain the measurements described above. For example, the heart can be accessed by traditional surgical approaches, such as a sternotomy or a thoracotomy. Alternatively, the heart can be accessed through minimally invasive heart valve surgery, such as an upper mini-sternotomy (for aortic valve replacement) or a lower mini-sternotomy (for mitral valve replacement).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of sizing a heart valve annulus for implant of a prosthetic heart valve, comprising:
   accessing a patient's heart valve annulus;
   placing an orifice-expanding device of a sizing apparatus into the annulus;
   expanding the orifice-expanding device to a desired pressure against the annulus such that the annulus expands, wherein the desired pressure is between about 250 mmHg and 500 mmHg;
   measuring a dimension of the expanded annulus; and
   selecting a prosthetic heart valve based on the measured dimension of the annulus.

2. The method of claim 1, wherein the method further comprises implanting the heart valve in the annulus.

3. The method of claim 1, wherein the act of measuring a dimension of the expanded annulus is accomplished while the orifice-expanding device is in the expanded annulus.

4. The method of claim 3, wherein the act of measuring a dimension of the expanded annulus comprises reading visual indicia on the sizing apparatus and recording the measured dimension.

5. The method of claim 3, wherein the sizing apparatus comprises a coiled member surrounding at least a portion of the orifice-expanding device and which uncoils upon expansion of the orifice-expanding device, the coiled member having a first end and a second end, the first end being fixed relative to the orifice-expanding device, the coiled member having visual indicia on a surface of the coiled member, and wherein the act of measuring a dimension of the expanded annulus comprises observing the position of the second end of the coiled member relative to the visual indicia.

6. The method of claim 3, wherein the sizing apparatus comprising an elongated shaft and a movable indicator coupled to the orifice-expanding device and operable to move longitudinally of the shaft upon expansion of the orifice-expanding device, wherein the act of measuring a dimension of the expanded annulus comprises observing the position of the movable indicator relative to a location on the shaft.

7. The method of claim 1, wherein the act of measuring a dimension of the expanded annulus is accomplished after the orifice-expanding device is removed from the body.

8. The method of claim 7, further comprising retaining the orifice-expanding device in an expanding state after the act of expanding the orifice-expanding device and removing the orifice-expanding device from the body in its expanded state in order to measure the dimension of the expanded annulus.

9. The method of claim 1, wherein the desired pressure exerted by the orifice-expanding device is at least the physiological pressure experienced by the annulus at its greatest diameter during the cardiac cycle.

10. The method according to claim 1, wherein the orifice-expanding device is a balloon and the act of expanding comprises inflating the balloon to expand the annulus.

11. The method according to claim 1, wherein the orifice-expanding device comprises one or more strain gauges and the method further comprises measuring the strain on the orifice-expanding device when it is expanded and determining the pressure exerted against the annulus by the orifice-expanding device from the measured strain.

12. The method according to claim 1, wherein the orifice-expanding device comprises a non-cylindrical outer surface that generally corresponds to the shape of the annulus.

13. The method of claim 1, wherein the desired pressure is about 350 mmHg.

14. The method of claim 1, wherein the desired pressure approximates the pressure the annulus will experience during expansion of an expandable prosthetic valve.

15. A method of sizing a heart valve annulus for implant of a prosthetic heart valve, comprising:
   radially expanding a patient's heart valve annulus using a desired pressure on the annulus which is equal to at least the physiological pressure experienced by the annulus at its greatest diameter during the cardiac cycle, wherein the desired pressure is between about 250 mmHg and 500 mmHg;
   measuring a dimension of the expanded annulus; and
   selecting a prosthetic heart valve based on the measured dimension of the annulus.

16. The method of claim 15, wherein the method further comprises implanting the heart valve in the annulus.

17. The method of claim 16, wherein the act of radially expanding the annulus comprises inserting an orifice-expanding device in the heart valve annulus and expanding the orifice-expanding device to expand the annulus, and the method further comprises determining the pressure exerted by the orifice-expanding device against the annulus in order to expand the annulus to the desired pressure.

18. The method of claim 16, wherein the act of radially expanding the annulus comprises inserting an orifice-expanding device in the heart valve annulus and expanding the orifice-expanding device to expand the annulus, the act of indicating comprises indicating the diameter of the expanded annulus after it is expanded by the orifice expanding device, and the act of implanting the heart valve comprises inserting the heart valve in the annulus and expanding the heart valve to expand the annulus and anchor the heart valve in the expanded annulus, wherein the diameter of the expanded annulus after implanting the heart valve is approximately the same as the diameter of the annulus after it was expanded by the orifice-expanding device.

19. The method of claim 17, wherein the act of implanting the heart valve comprises inserting the heart valve in the annulus and expanding the heart valve to expand the annulus and anchor the heart valve in the expanded annulus, wherein the pressure exerted by the expanded heart valve is approximately the same as the desired pressure.

20. The method of claim 15, wherein the act of radially expanding the annulus comprises inserting an orifice-expanding device in the heart valve annulus and expanding the orifice-expanding device to expand the annulus, and wherein the orifice-expanding device comprises a non-cylindrical outer surface that generally corresponds to the shape of the annulus.

21. The method of claim 20, wherein the non-cylindrical outer surface is a tri-lobe configuration that corresponds with the shape of an aortic valve annulus.

22. The method of claim 15, wherein the annulus is the aortic valve annulus, and the pressure that occurs when the annulus is at its greatest diameter occurs at the end of systole.

23. The method of claim 15, wherein the desired pressure is about 350 mmHg.

24. The method of claim 15, wherein the desired pressure is the physiological pressure experienced by the annulus at its greatest diameter during the cardiac cycle plus an additional amount of pressure to ensure that the measured dimension of the annulus corresponds to a valve size that will provide a proper interference fit with the annulus.

25. The method of claim 15, wherein the desired pressure approximates the pressure the annulus will experience during expansion of an expandable prosthetic valve.

26. The method of claim 12, wherein the non-cylindrical outer surface is a tri-lobe configuration that corresponds with the shape of an aortic valve annulus.

27. The method of claim 9, wherein the annulus is the aortic valve annulus, and the pressure that occurs when the annulus is at its greatest diameter occurs at the end of systole.

28. The method of claim 27, wherein the desired pressure is the physiological pressure experience by the annulus at its greatest diameter during the cardiac cycle plus an additional amount of pressure to ensure that the measured dimension of the annulus corresponds to a valve size that will provide a proper interference fit with the annulus.

\* \* \* \* \*